(12) United States Patent
Matsui et al.

(10) Patent No.: US 10,390,742 B2
(45) Date of Patent: Aug. 27, 2019

(54) NON-INVASIVE MONITOR FOR MEASURING REGIONAL SATURATION OF OXYGEN

(71) Applicant: KOHKEN MEDICAL CO., LTD., Tokyo (JP)

(72) Inventors: Eiichi Matsui, Tokyo (JP); Mitsuo Matsui, Tokyo (JP); Yasuo Nakajima, Tokyo (JP)

(73) Assignee: KOHKEN MEDICAL CO., LTD., Tokyo (JP)

( * ) Notice: Subject to any disclaimer, the term of this patent is extended or adjusted under 35 U.S.C. 154(b) by 263 days.

(21) Appl. No.: 15/112,918

(22) PCT Filed: Jan. 14, 2015

(86) PCT No.: PCT/JP2015/050823
§ 371 (c)(1),
(2) Date: Jul. 20, 2016

(87) PCT Pub. No.: WO2015/115182
PCT Pub. Date: Aug. 6, 2015

(65) Prior Publication Data
US 2016/0338630 A1 Nov. 24, 2016

(30) Foreign Application Priority Data
Jan. 29, 2014 (JP) .................. 2014-014706

(51) Int. Cl.
*A61B 5/00* (2006.01)
*A61B 5/1455* (2006.01)

(52) U.S. Cl.
CPC ........ *A61B 5/14553* (2013.01); *A61B 5/6803* (2013.01); *A61B 5/14552* (2013.01); *A61B 5/684* (2013.01); *A61B 2562/166* (2013.01)

(58) Field of Classification Search
CPC ... A61B 5/6803; A61B 5/6814; A61B 5/6831; A61B 5/684; A61B 5/14553; A61B 2562/166; G02B 27/017; G02B 27/0176
See application file for complete search history.

(56) References Cited

U.S. PATENT DOCUMENTS 2,935,910 A * 5/1960 Schmidt ............... G02B 25/004
351/156
4,896,375 A * 1/1990 Colucci .................. A42B 1/062
2/12

(Continued)

FOREIGN PATENT DOCUMENTS

JP 2009-240454 A 10/2009
JP 2011-135986 A 7/2011

(Continued)

OTHER PUBLICATIONS

International Search Report in corresponding App No. PCT/JP2015/050823 dated Apr. 7, 2015.

(Continued)

*Primary Examiner* — Eric F Winakur
*Assistant Examiner* — Abid A Mustansir
(74) *Attorney, Agent, or Firm* — Workman Nydegger

(57) ABSTRACT

A non-invasive monitor for measuring regional saturation of oxygen includes a sensor unit containing a printed circuit board on which a light emitting unit and a light receiving unit are mounted; a main body unit; a sensor holder for holding the sensor unit while the light emitting unit and the light receiving unit are disposed in an aperture portion; a sensor pressing board; a connecting unit for electrically connecting the sensor unit and the main body unit; and a headband. The light emitting unit and the light receiving unit are disposed such that a light emitting surface and a light receiving surface face the forehead-side, and a part or the whole of the forehead-side surface of the sensor unit is on (Continued)

the same surface as the forehead-side surface of the sensor holder or protrudes from the forehead-side surface of the sensor holder toward the forehead-side.

11 Claims, 14 Drawing Sheets

(56) References Cited

U.S. PATENT DOCUMENTS

| | | | |
|---|---|---|---|
| 2002/0161290 A1* | 10/2002 | Chance | A61B 5/14551 600/323 |
| 2003/0182718 A1* | 10/2003 | Lee | A44B 11/223 2/452 |
| 2005/0283082 A1* | 12/2005 | Geddes | A61B 5/0059 600/485 |
| 2009/0209836 A1 | 8/2009 | Niwayama | |
| 2009/0247839 A1 | 10/2009 | Ninomiya et al. | |
| 2010/0073582 A1* | 3/2010 | Konno | G02F 1/133308 348/794 |
| 2010/0076276 A1* | 3/2010 | Gilland | A61B 5/1455 600/301 |
| 2010/0130840 A1* | 5/2010 | Isaacson | A61B 5/14553 600/323 |
| 2012/0101349 A1* | 4/2012 | DelloStritto | A61B 5/14552 600/324 |
| 2012/0150047 A1* | 6/2012 | Terumoto | A61B 5/02427 600/479 |
| 2013/0158372 A1* | 6/2013 | Haisley | A61B 5/1455 600/310 |
| 2015/0051464 A1 | 2/2015 | Ozaki et al. | |
| 2015/0094552 A1* | 4/2015 | Golda | A61B 5/04325 600/336 |

FOREIGN PATENT DOCUMENTS

| | | |
|---|---|---|
| JP | 2012-045168 A | 3/2012 |
| JP | 5062698 B2 | 10/2012 |
| JP | 2013-170881 A | 7/2013 |

OTHER PUBLICATIONS

Translation of Written Opinion of the International Searching Authority dated Jul. 4, 2015 for PCT/JP2015/050823.

Preliminary Report on Patentability for PCT/JP2015/050823 dated Aug. 2, 2016 (Aug. 2, 2016).

* cited by examiner

[Fig.1]
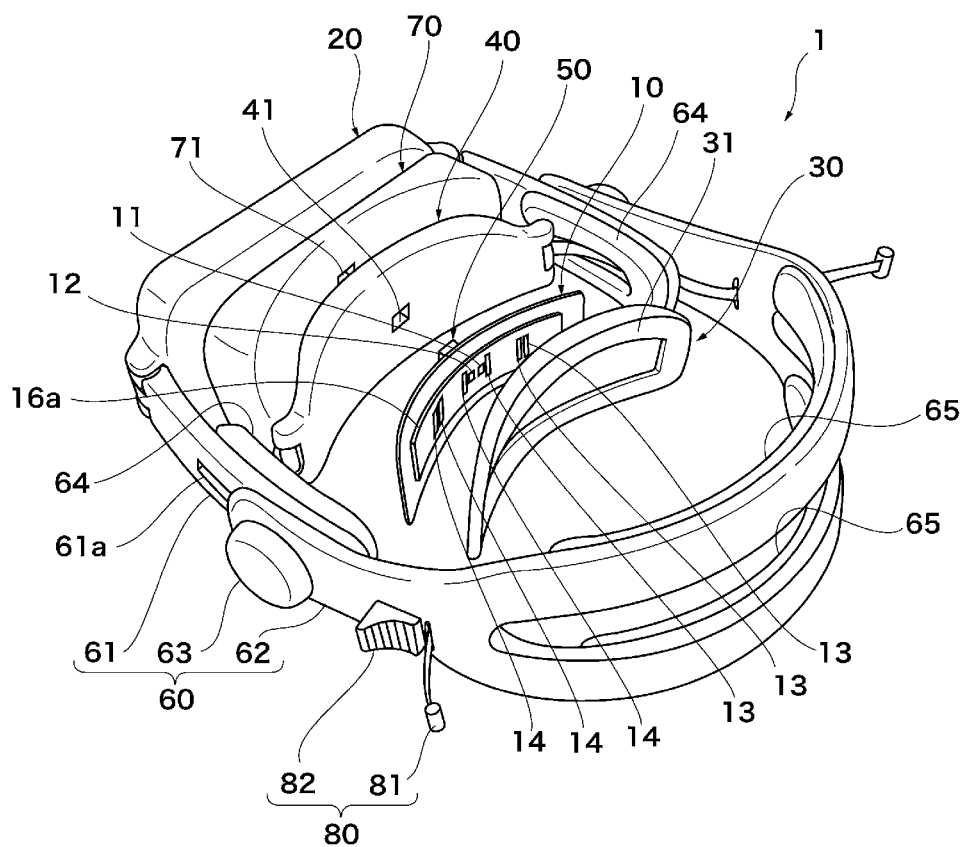

[Fig.2]
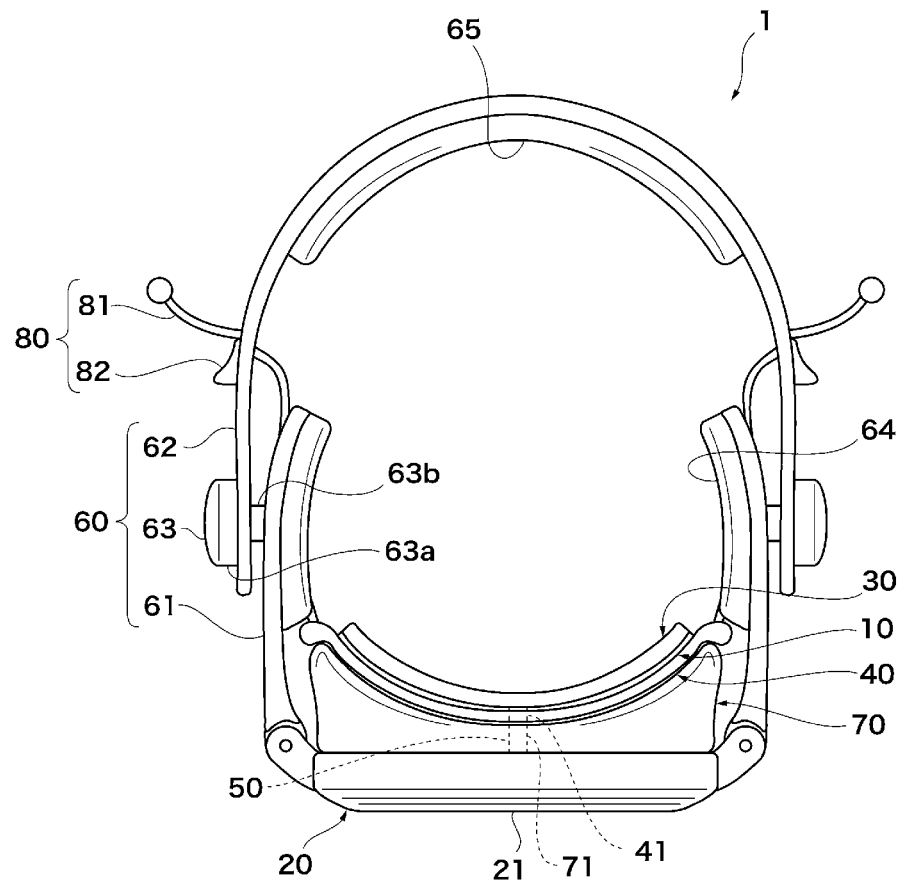
[Fig.3]
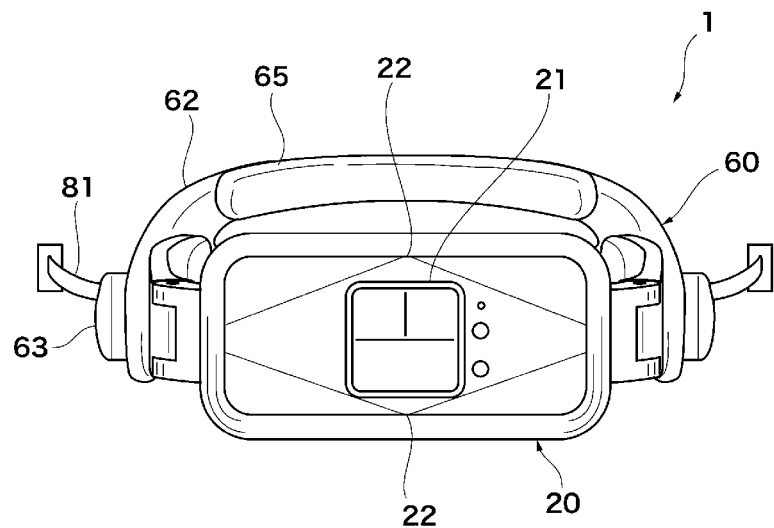

[Fig.4]
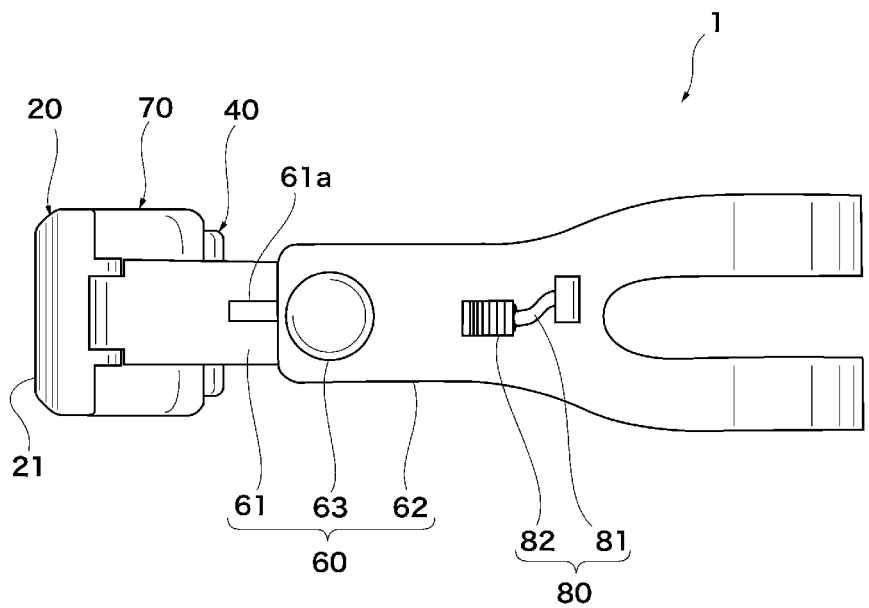
[Fig.5]
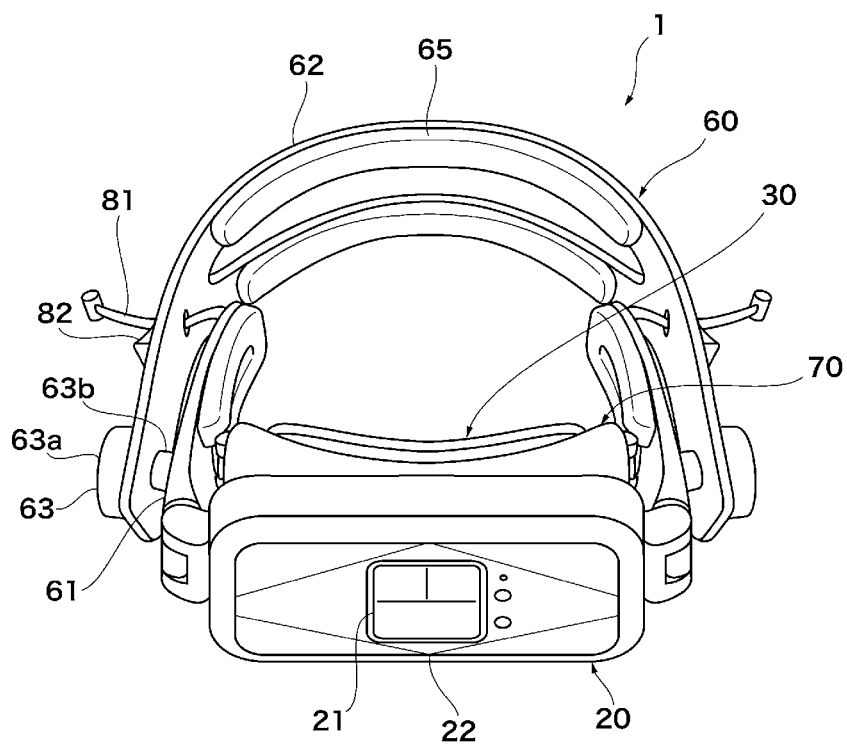

[Fig.6]
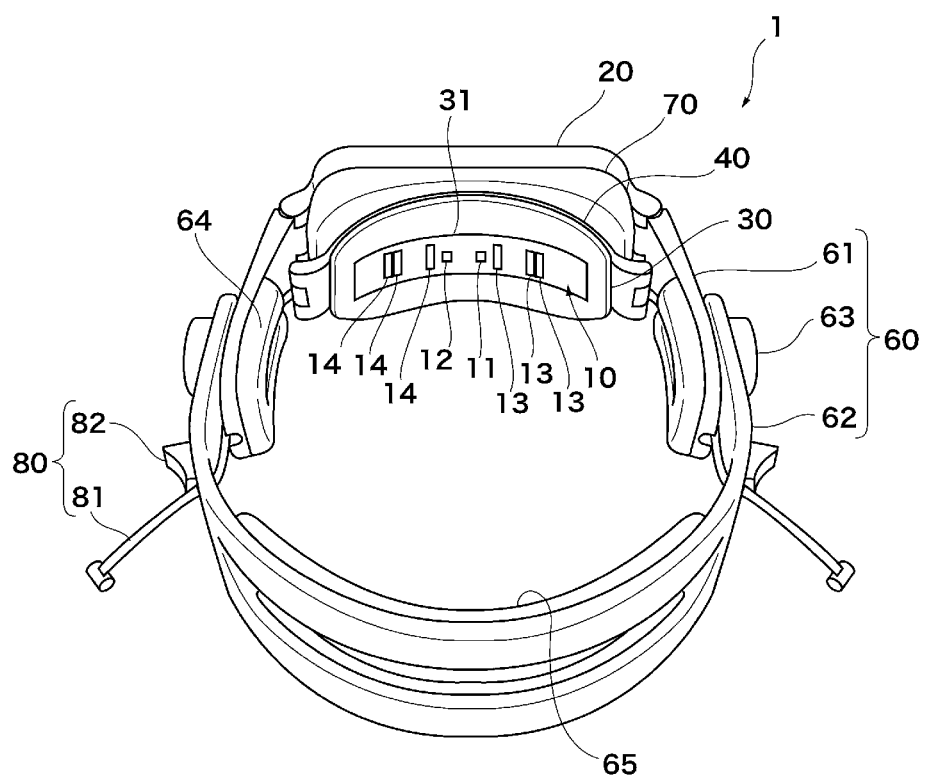

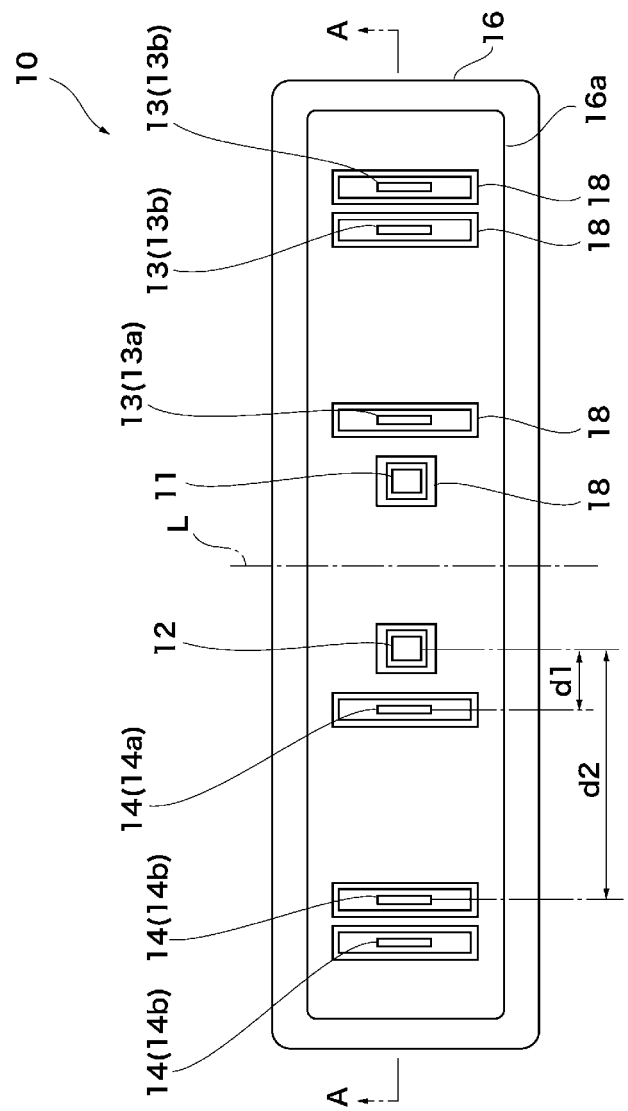
[Fig.7]

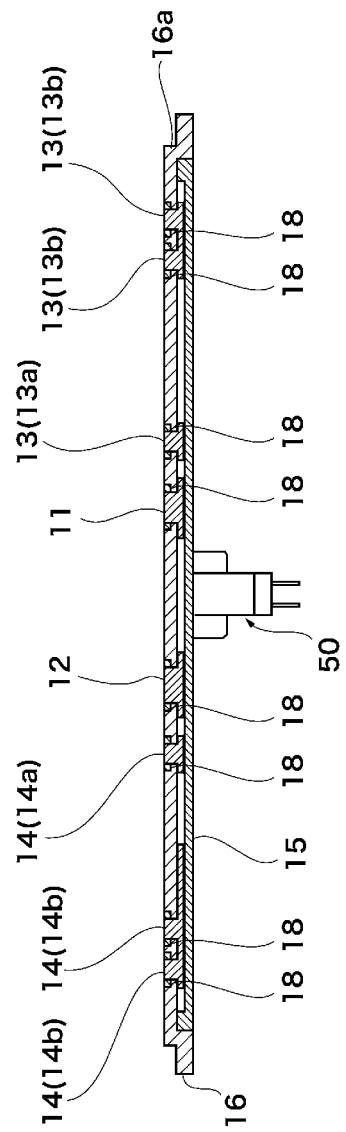
[Fig.8]

[Fig.9]
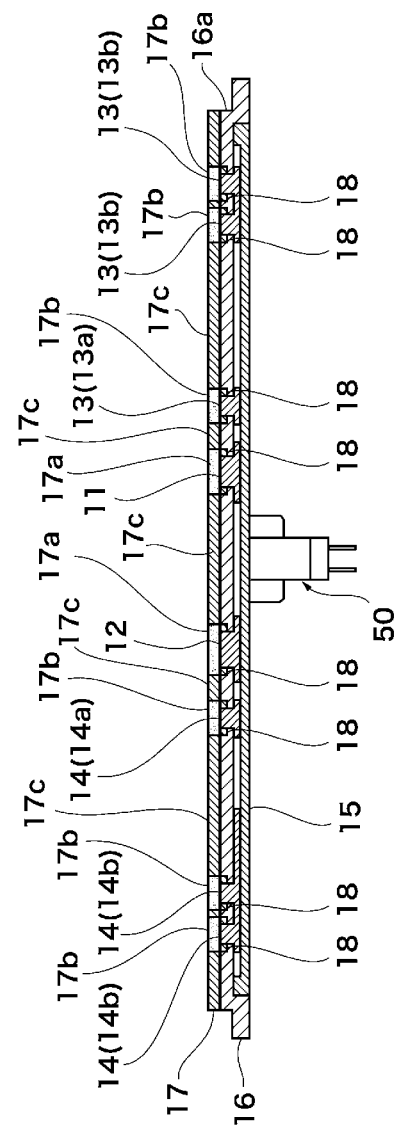

[Fig.10]
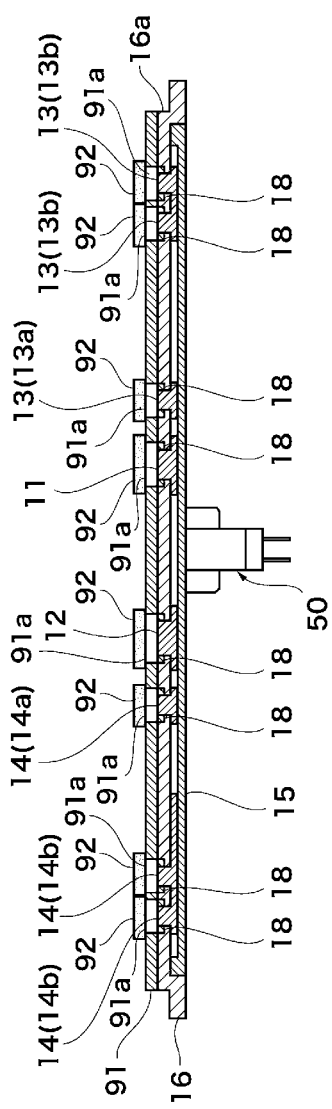

[Fig.11]
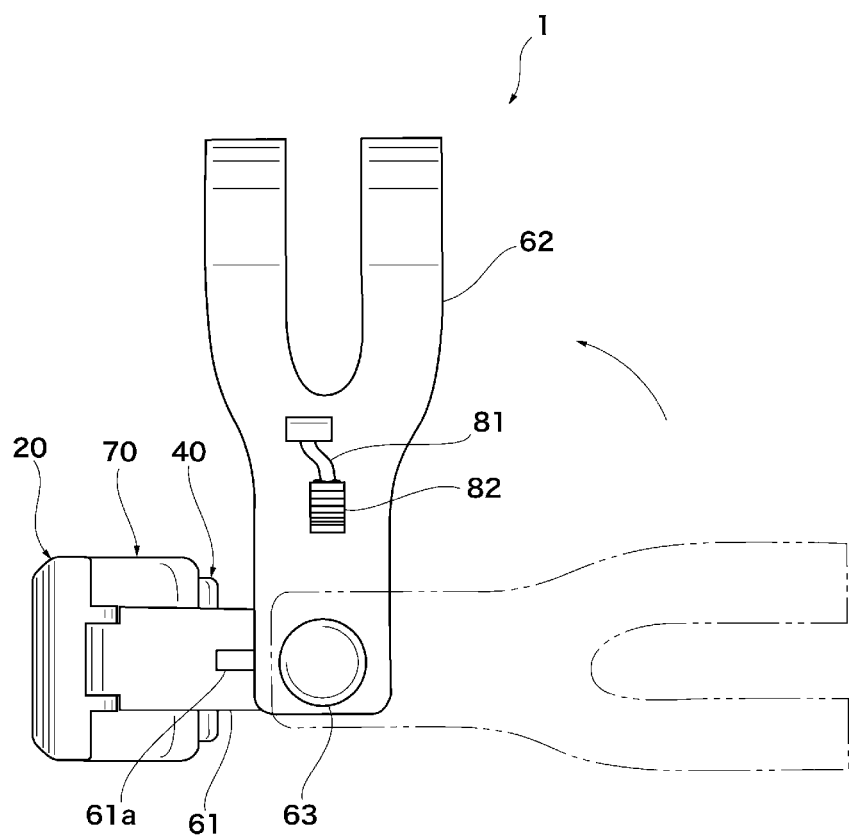

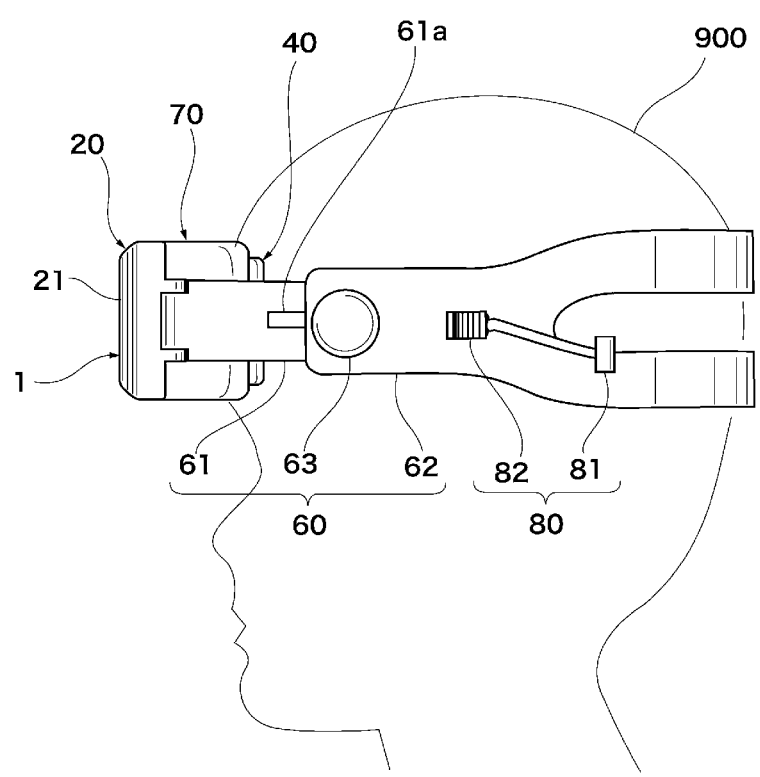
[Fig.12]

[Fig.13]
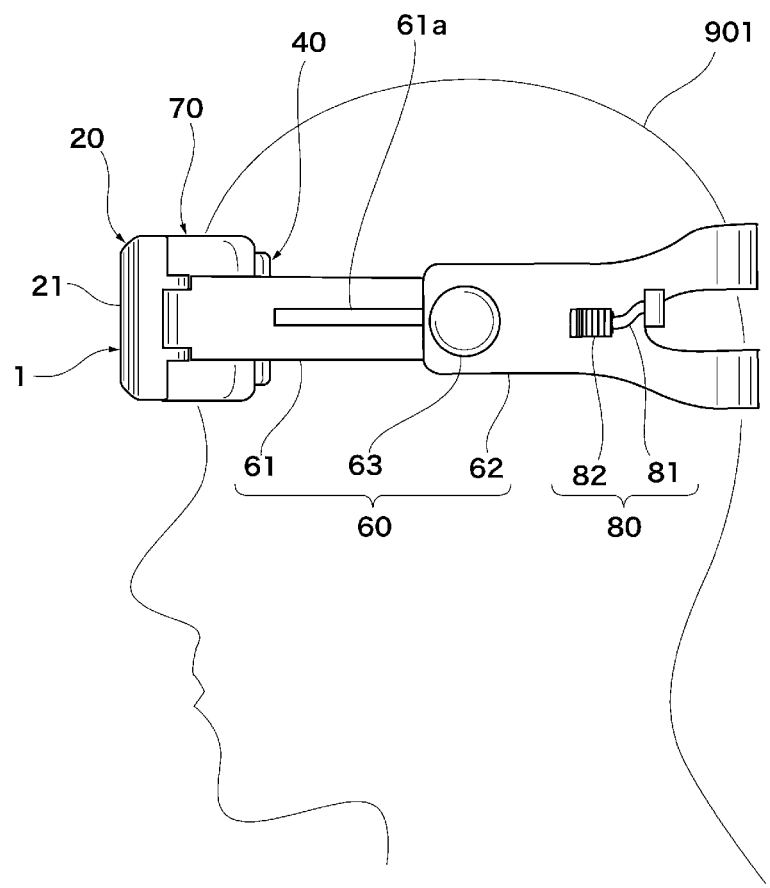

[Fig.14]
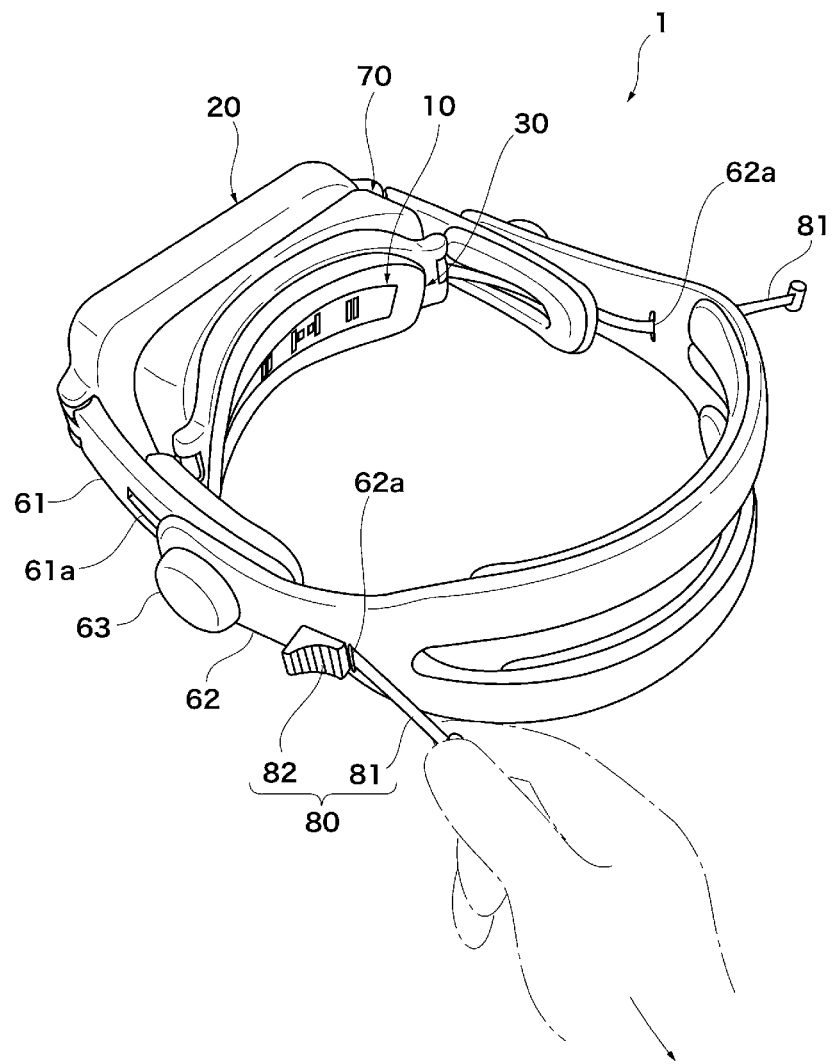

[Fig.15]
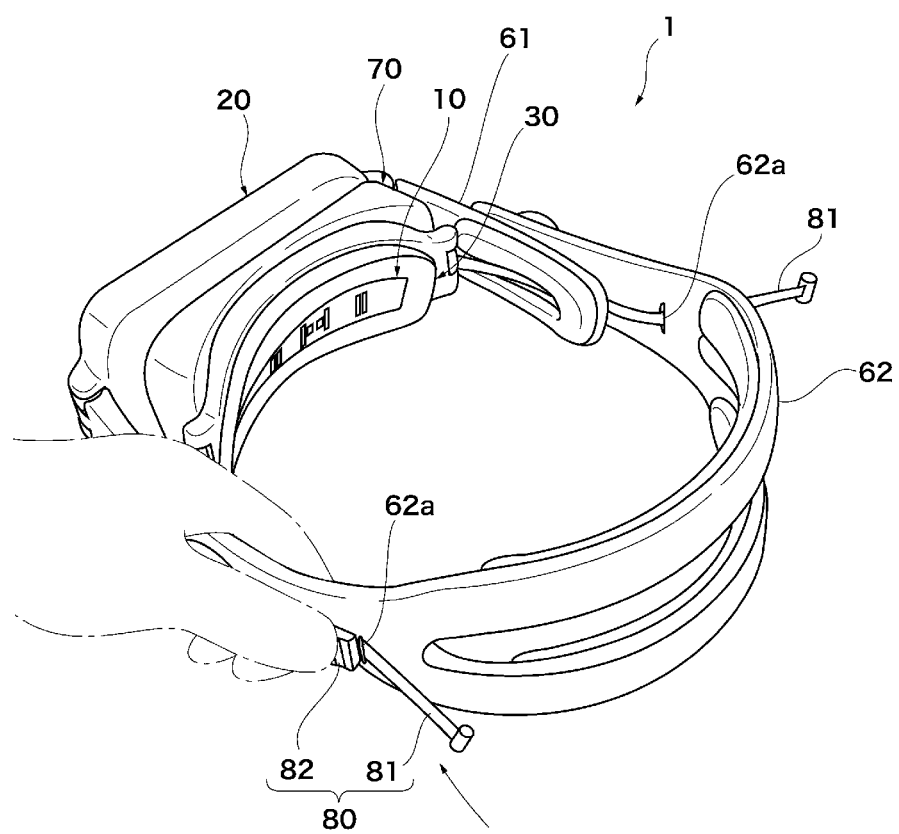

[Fig.16]
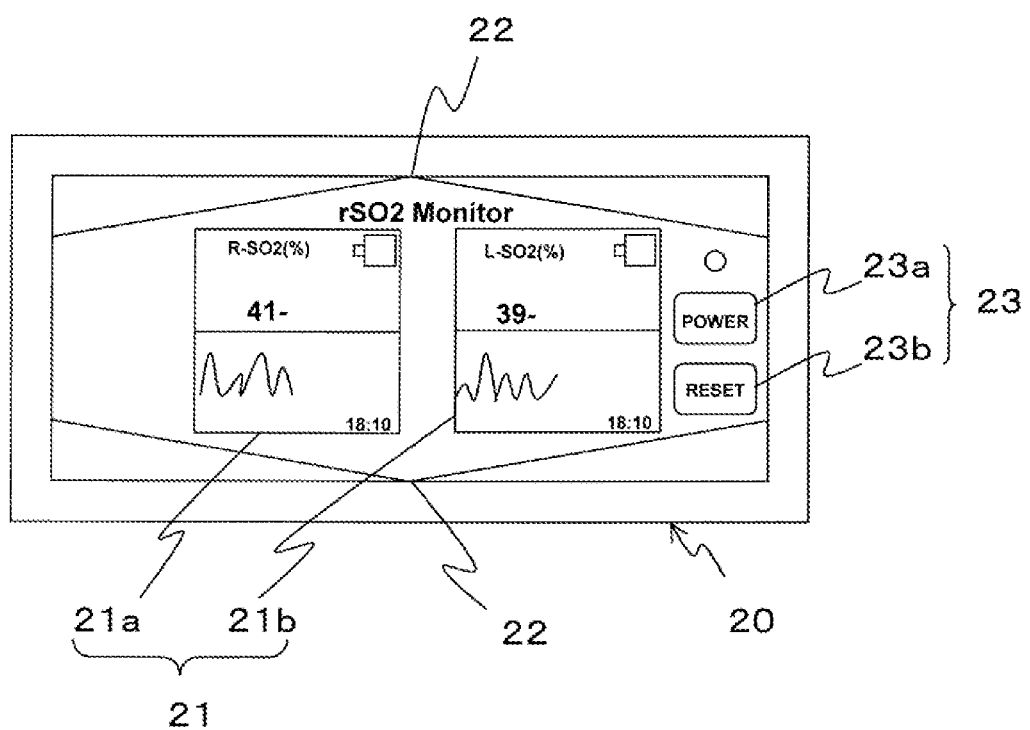

NON-INVASIVE MONITOR FOR MEASURING REGIONAL SATURATION OF OXYGEN

CROSS REFERENCE TO RELATED APPLICATIONS

This application is a U.S. Nationalization of PCT Application Number PCT/JP2015/050823, filed on Jan. 14, 2015, which claims priority to JP Patent Application No. 2014-014706, filed on Jan. 29, 2014, the entireties of which are incorporated herein by reference.

TECHNICAL FIELD

The present invention relates to a non-invasive monitor for measuring regional saturation of oxygen, which is light and compact, and has excellent portability and handleability.

BACKGROUND ART

In recent years, particularly in emergency medicine, it has come to be known to significantly improve a rehabilitation rate of a cardiac arrest patient by emergency life-saving measures by a doctor or an emergency medical technician while a regional saturation of oxygen ($rSO_2$) of the cardiac arrest patient is monitored using a near-infrared ray (for example, refer to Patent Literatures 1 and 2). Generally, for example, as illustrated in FIG. 1 of Patent Literature 2, a structure of an apparatus for monitoring a regional saturation of oxygen ($rSO_2$) using a near-infrared ray is separated into a probe unit attached to the forehead of a patient's head and an apparatus main body unit having a circuit board for analyzing a signal from the probe unit and a display unit for displaying an analysis result integrated, and the probe unit and the apparatus main body unit are connected with a long signal cable.

CITATION LIST

Patent Literature

[Patent Literature 1] JP 5062698 B1
[Patent Literature 2] JP 2013-170881 A

SUMMARY OF INVENTION

Technical Problem

Such a structure of an apparatus as illustrated in FIG. 1 of Patent Literature 2 does not particularly cause a problem in a hospital for receiving a cardiac arrest patient. However, in an emergency site such as outside a hospital or in an emergency vehicle, a working space and personnel are limited. Therefore, when an operator such as a doctor or an emergency medical technician performs emergency life-saving measures in an emergency life-saving site, an apparatus with a probe unit and an apparatus main body unit separated has a problem in terms of size, mass, easiness of handling, or the like due to hindrance of space of the site or narrowness of the space. Therefore, in the emergency life-saving site, appearance of a non-invasive monitor for measuring regional saturation of oxygen in which a probe unit and an apparatus main body unit are integrated, which is light and compact, and has excellent portability and excellent handleability to make an operator handle the monitor easily, has been desired.

An object of the present invention is to provide a non-invasive monitor for measuring regional saturation for oxygen which is light and compact, and has excellent portability and excellent handleability to make an operator handle the monitor easily.

Solution to Problem

A non-invasive monitor for measuring regional saturation of oxygen according to the present invention measures an oxygen saturation of a brain blood stream continuously in a non-invasive manner by mounting the monitor on a person's head, and includes at least a sensor unit containing a printed circuit board on which a light emitting unit for irradiating a surface of the forehead of the head with light of 650 to 1000 nm and a light receiving unit for receiving light which has been emitted by the light emitting unit and has propagated inside the head are mounted; a main body unit disposed in front of the forehead when being mounted on the head, containing a computation processing unit for calculating a mixed oxygen saturation of the brain blood based on a detection signal detected by the sensor unit, a display unit for displaying a computation processing result by the computation processing unit, and a power source unit for supplying power to the sensor unit, the computation processing unit, and the display unit; a sensor holder for holding the sensor unit while the light emitting unit and the light receiving unit are disposed in an aperture portion, having a board shape abutting on the forehead and containing the aperture portion penetrating in a board thickness direction thereof; a sensor pressing board for holding the sensor unit toward the sensor holder, disposed between the sensor unit and the main body unit; a connecting unit for electrically connecting the sensor unit and the main body unit; and a headband for mounting the main body unit on the head detachably, characterized in that the light emitting unit and the light receiving unit are disposed such that a light emitting surface of the light emitting unit and a light receiving surface of the light receiving unit face the forehead-side, and a part or the whole of the forehead-side surface of the sensor unit is on the same surface as a forehead-side surface of the sensor holder or protrudes from the forehead-side surface of the sensor holder toward the forehead-side.

The non-invasive monitor for measuring regional saturation of oxygen according to the present invention preferably further includes a cushion interposed between the main body unit and the sensor pressing board. By bringing the sensor unit into closer contact with the forehead, entrance of light from the outside into the light receiving unit can be suppressed, and measurement can be performed with higher accuracy.

In the non-invasive monitor for measuring regional saturation of oxygen according to the present invention, preferably, the sensor unit includes a right light emitting unit and a left light emitting unit as the light emitting unit and a right light receiving unit and a left light receiving unit as the light receiving unit, the left light receiving unit, the left light emitting unit, the right light emitting unit, and the right light receiving unit are disposed in this order in a lateral direction of the forehead, the left light emitting unit and the right light emitting unit are disposed in linear symmetry with a virtual straight line between the left light emitting unit and the right light emitting unit as a symmetric axis, and the left light receiving unit and the right light emitting unit are disposed in linear symmetry with the virtual straight line as a symmetric axis. The oxygen saturation of the right brain and left brain can be measured at the same time.

In the non-invasive monitor for measuring regional saturation of oxygen according to the present invention, preferably, the main body unit has a center mark, and the position of the center mark in a lateral direction of the forehead is on the virtual straight line. An operator can easily confirm the positions of the right light emitting unit and the left light emitting unit. By mounting the monitor by matching the center mark with the center portion in a lateral direction of the forehead of a patient, the oxygen saturation of the right brain and left brain can be measured more securely and more accurately.

In the non-invasive monitor for measuring regional saturation of oxygen according to the present invention, preferably, the headband includes an inner headband connected to the main body unit, an outer headband connected to the outside of the inner headband, and a connecting portion connecting the outer headband to the inner headband so as to be able to be tightened or loosened, the inner headband includes a slide groove portion, the connecting portion includes a shaft portion engaging with the slide groove portion, and the headband can lift the outer headband around the shaft portion and can adjust the position of the outer headband by sliding the shaft portion along the slide groove portion and matching the headband with the size of the head. The monitor can be mounted on a patient more easily. An operator alone can mount the monitor due to the lifting type outer headband.

The non-invasive monitor for measuring regional saturation of oxygen according to the present invention preferably further includes a tightening tool connected to the sensor pressing board. By bringing the sensor unit into closer contact with the forehead, entrance of light from the outside into the light receiving unit can be suppressed, and measurement can be performed with higher accuracy.

In the non-invasive monitor for measuring regional saturation of oxygen according to the present invention, the connecting unit is preferably a connector. By no use of a cable, a problem that work is hindered because a cable is caught does not occur. The size of the non-invasive monitor for measuring regional saturation of oxygen can be smaller. The connector also serves as a fixing tool for fixing the sensor unit to the main body unit.

In the non-invasive monitor for measuring regional saturation of oxygen according to the present invention, preferably, the sensor unit includes a covering portion for covering a part or the whole of the forehead-side surface of the sensor unit, and the covering portion includes a silicone portion made of silicone and transmitting the light at least in a portion covering the light emitting surface-side of the light emitting unit and a portion covering the light receiving surface-side of the light receiving unit. A contaminant adhering to the light emitting surface and the light receiving surface can be wiped off more easily. By replacing the covering portion, it is possible to keep the light emitting surface and the light receiving surface clean all the time.

In the non-invasive monitor for measuring regional saturation of oxygen according to the present invention, preferably, the covering portion includes a light transmission hindering portion at least between the silicone portion covering the light emitting unit and the silicone portion covering the light receiving unit, and the transmittance of the light in terms of a thickness of 1 mm in the light transmission hindering portion is one tenth or less with respect to the transmittance of the light in terms of a thickness of 1 mm in the silicone portion. By transmission of light not propagating inside the head through the silicone portion, entrance of the light into the light receiving unit can be suppressed, and measurement can be performed with higher accuracy.

In the non-invasive monitor for measuring regional saturation of oxygen according to the present invention, the sensor unit preferably includes a light receiving unit for a shallow portion and a light receiving unit for a deep portion as the light receiving unit. Measurement can be performed with higher accuracy.

Advantageous Effects of Invention

The present invention can provide a non-invasive monitor for measuring regional saturation of oxygen which is light and compact, and has excellent portability and excellent handleability to make an operator handle the monitor easily.

BRIEF DESCRIPTION OF DRAWINGS

FIG. 1 exemplifies a non-invasive monitor for measuring regional saturation of oxygen according to the present embodiment, and is a perspective view illustrating the monitor partially exploded.

FIG. 2 is a plan view exemplifying the non-invasive monitor for measuring regional saturation of oxygen according to the present embodiment.

FIG. 3 is a front view exemplifying the non-invasive monitor for measuring regional saturation of oxygen according to the present embodiment.

FIG. 4 is a right side view exemplifying the non-invasive monitor for measuring regional saturation of oxygen according to the present embodiment.

FIG. 5 exemplifies the non-invasive monitor for measuring regional saturation of oxygen according to the present embodiment, and is a perspective view seen from the upper front face.

FIG. 6 exemplifies the non-invasive monitor for measuring regional saturation of oxygen according to the present embodiment, and is a perspective view seen from the upper rear face.

FIG. 7 is a plan view exemplifying a sensor unit.

FIG. 8 is a cross sectional view cut along line A-A in FIG. 7.

FIG. 9 is a cross sectional view illustrating a first example of a covering portion.

FIG. 10 is a cross sectional view illustrating a second example of the covering portion.

FIG. 11 is a diagram illustrating a state in which an outer headband is lifted.

FIG. 12 is a diagram illustrating a state in which the monitor is mounted on a person having a small head.

FIG. 13 is a diagram illustrating a state in which the monitor is mounted on a person having a large head.

FIG. 14 is a diagram illustrating a state in which a tightening tool is tightened.

FIG. 15 is a diagram illustrating a state in which the tightening tool is loosened.

FIG. 16 is a schematic diagram illustrating a modification example of a main body unit.

DESCRIPTION OF EMBODIMENTS

Next, the present invention will be described in detail by describing embodiments, but the present invention is not construed as being limited to description thereof. As long as an effect of the present invention is exhibited, the embodiments may be modified variously.

A non-invasive monitor for measuring regional saturation of oxygen 1 according to the present embodiment measures an oxygen saturation of a brain blood stream continuously in a non-invasive manner by mounting the monitor on a person's head, and includes at least, as illustrated in FIG. 1, a sensor unit 10 containing a printed circuit board on which light emitting units 11,12 for irradiating a surface of the forehead of the head with light of 650 to 1000 nm and light receiving units 13,14 for receiving light which has propagated inside the head of the light emitted by the light emitting units 11,12 are mounted; as illustrated in FIGS. 2 to 5, a main body unit 20 disposed in front of the forehead when being mounted on the head, containing a computation processing unit (not illustrated) for calculating a mixed oxygen saturation of the brain blood based on a detection signal detected by the sensor unit 10, a display unit 21 for displaying a computation processing result by the computation processing unit, and a power source unit (not illustrated) for supplying power to the sensor unit 10, the computation processing unit, and the display unit 21; as illustrated in FIGS. 1 and 6, a sensor holder 30 for holding the sensor unit 10 while the light emitting units 11,12 and the light receiving units 13,14 are disposed in an aperture portion 31, having a board shape abutting on the forehead and containing the aperture portion 31 penetrating in a board thickness direction thereof; a sensor pressing board 40 for holding the sensor unit 10 toward the sensor holder 30, disposed between the sensor unit 10 and the main body unit 20; a connecting unit 50 for electrically connecting the sensor unit 10 and the main body unit 20; and a headband 60 for mounting the main body unit 20 on the head detachably. The light emitting units 11,12 and the light receiving units 13,14 are disposed such that light emitting surfaces of the light emitting units 11,12 and light receiving surfaces of the light receiving units 13,14 face the forehead-side and a part or the whole of the forehead-side surface of the sensor unit 10 is on the same surface as a forehead-side surface of the sensor holder 30 or protrudes from the forehead-side surface of the sensor holder 30 toward the forehead-side.

The non-invasive monitor for measuring regional saturation of oxygen 1 according to the present embodiment measures an oxygen saturation ($rSO_2$) of a brain blood stream continuously in a non-invasive manner by near-infrared spectroscopy (NIRS).

FIG. 7 is a plan view exemplifying a sensor unit. FIG. 8 is a cross sectional view cut along line A-A in FIG. 7. The sensor unit 10 is a board-shaped member which can be bent according to the shape of the forehead. The sensor unit 10 includes a printed circuit board 15 as illustrated in FIG. 8.

In the printed circuit board 15 electronic components such as the light emitting units 11,12 and the light receiving units 13,14 are mounted on a flexible wiring board. For example, the flexible wiring board has a structure obtained by laminating a substrate film layer of a polyester film and a polyimide film, an adhesive layer, and a conductive foil layer such as copper foil sequentially. The present invention is not limited by the structure of the flexible wiring board. In a mounted surface of the printed circuit board 15, a portion other than the light emitting units 11,12 or the light receiving units 13,14 is preferably covered with a probe cover 16. A material of the probe cover 16 is not particularly limited, but for example, is an elastomer such as silicone rubber. The probe cover 16 preferably has a protrusion 16a formed by making a region including the light emitting units 11,12 and the light receiving units 13,14 relatively protrude compared with the other regions. As illustrated in FIG. 6, by fitting the protrusion 16a into the aperture portion 31 of the sensor holder 30, the sensor unit 10 can be held by the sensor holder 30 more firmly. The probe cover 16 may be disposed on a rear surface of the mounted surface of the printed circuit board 15 in addition to the mounted surface.

For example, each of the light emitting units 11,12 is a light emitting element such as a light emitting diode (LED). The light emitting units 11,12 are disposed such that light emitting surfaces thereof face the forehead-side. The light emitting units 11,12 are preferably surrounded by a frame portion 18. By bringing the frame portion 18 into close contact with the forehead, the forehead can be irradiated with light emitted by the light emitting units 11,12 more efficiently. The light emitted by the light emitting units 11,12 is near-infrared light of 650 to 1000 nm. The light emitting units 11,12 can preferably output two or more kinds of light having different wavelengths sequentially. For example, the two or more kinds of light having different wavelengths is light having two wavelengths of 730 nm and 810 nm.

For example, each of the light receiving units 13,14 is a light receiving element such as a photodiode. The light receiving units 13,14 are disposed such that light receiving surfaces thereof face the forehead-side. The light receiving units 13,14 are preferably surrounded by the frame portion 18. After the light emitted by the light emitting units 11,12 propagates inside the head, the light receiving units 13,14 can receive the light more efficiently by bringing the frame portion 18 into close contact with the forehead.

The sensor unit 10 preferably includes light receiving units for a shallow portion 13a and 14a and light receiving units for a deep portion 13b and 14b as the light receiving units 13,14. By including the light receiving units for a shallow portion 13a and 14a and the light receiving units for a deep portion 13b and 14b, measurement can be performed with higher accuracy. A distance d2 between the light receiving units for a deep portion 13b and 14b and the light emitting units 11,12 is preferably longer than a distance d1 between the light receiving units for a shallow portion 13a and 14a and the light emitting units 11,12. The distance d1 between the light receiving units for a shallow portion 13a and 14a and the light emitting units 11,12 is a distance of light from emission by the light emitting units 11,12 until arrival at a surface of the forehead through a shallow layer of the brain, and is for example, preferably 0.1 mm or more and 35 mm or less, and more preferably 0.5 mm or more and 30 mm or less. The distance d2 between the light receiving units for a deep portion 13b and 14b and the light emitting units 11,12 is a distance of light from emission by the light emitting units 11,12 until arrival at a surface of the forehead through a deep layer of the brain, and is for example, preferably more than 35 mm and 60 nm or less, and more preferably 40 mm or more and 50 mm or less. The distances d1 and d2 are examples, and the present invention is not limited thereto. By disposing the two light receiving units for a deep portion 13b (14b) in parallel, the computation processing unit (not illustrated) can calculate a regional saturation of oxygen without creating a calibration curve.

As illustrated in FIG. 7, preferably, the sensor unit 10 includes a right light emitting unit 11 and a left light emitting unit 12 as the light emitting units 11,12 and a right light receiving unit 13 and a left light receiving unit 14 as the light receiving units 13,14, the left light receiving unit 14, the left light emitting unit 12, the right light emitting unit 11, and the right light receiving unit 13 are disposed in this order in a lateral direction of the forehead, the left light emitting unit 12 and the right light emitting unit 11 are disposed in linear symmetry with a virtual straight line L between the left light emitting unit 12 and the right light emitting unit 11 as a symmetric axis, and the left light receiving unit 14 and the right light receiving unit 13 are disposed in linear symmetry with the virtual straight line L as a symmetric axis. The oxygen saturation of the right brain and left brain can be measured at the same time.

FIG. 9 is a cross sectional view illustrating a first example of a covering portion. FIG. 9 illustrates a cross section of a position corresponding to line A-A in FIG. 7. Preferably, the sensor unit 10 includes a covering portion 17 for covering a part or the whole of the forehead-side surface of the sensor unit 10, and the covering portion 17 includes silicone portions 17a and 17b made of silicone and transmitting light at least in a portion covering the light emitting surface-sides of the light emitting units 11,12 and a portion covering the light receiving surface-sides of the light receiving units 13,14. By disposing the silicone portions 17a and 17b, it is possible to prevent a contaminant from adhering to the light emitting surface and the light receiving surface and to wipe off the contaminant adhering to the silicone portions 17a and 17b easily. By replacing the covering portion 17, it is possible to keep the light emitting surface and the light receiving surface clean all the time. FIG. 9 illustrates a form in which the covering portion 17 covers a surface of the protrusion 16a of the forehead-side surface of the sensor unit 10, but the present invention is not limited thereto, and for example, may be a form in which the covering portion 17 covers only the light emitting surfaces of the light emitting units 11,12 and the light receiving surfaces of the light receiving units 13,14 (not illustrated), or a form in which the covering portion 17 covers the whole of the forehead-side surface of the sensor unit 10. FIG. 9 illustrates a form in which the silicone portions 17a and 17b are disposed only on the light emitting units 11,12 and the light receiving units 13,14, but the silicone portions 17a and 17b may cover the whole of the forehead-side surface of the sensor unit 10. The silicone is, for example, silicone rubber. The transmittance of light emitted by the light emitting units 11,12 in terms of a thickness of 1 mm in the silicone portions 17a and 17b is preferably 60% or more, and more preferably 80% or more.

As illustrated in FIG. 9, preferably, the covering portion 17 includes a light transmission hindering portion 17c at least between the silicone portion 17a covering the light emitting units 11,12 and the silicone portion 17b covering the light receiving units 13,14, the transmittance of light emitted by the light emitting units 11,12 in terms of a thickness of 1 mm in the light transmission hindering portion 17c is one tenth or less with respect to the transmittance of the light in terms of a thickness of 1 mm in the silicone portions 17a and 17b. The transmittance of light is more preferably one twentieth or less. By disposition of the light transmission hindering portion 17c, entrance of light into the light receiving units 13,14 can be suppressed by transmission of light not propagating inside the head through the silicone portions 17a and 17b, and measurement can be performed with higher accuracy. The light transmission hindering portion 17c may be disposed between the silicone portions 17b covering the light receiving units 13,14 in addition to between the silicone portion 17a covering the light emitting units 11,12 and the silicone portion 17b covering the light receiving units 13,14. A preferable form of the covering portion 17 is, for example, a form in which the light transmission hindering portion 17c is a sheet provided with apertures in a ladder shape at positions corresponding to the light emitting units 11,12 and the light receiving units 13,14, and the silicone portions 17a and 17b are embedded into the apertures of the light transmission hindering portion 17c to form a shape of one sheet as a whole. In the form in which the silicone portions 17a and 17b and the light transmission hindering portion 17c form a shape of one sheet, the light transmission hindering portion 17c is preferably made of silicone rubber containing a black pigment such as carbon black.

FIG. 10 is a cross sectional view illustrating a second example of a covering portion. FIG. 10 illustrates a cross section of a position corresponding to line A-A in FIG. 7. As illustrated in FIG. 10, it is preferable that a covering portion includes a light transmission hindering portion 91 disposed on the forehead-side surface of the sensor unit 10 and provided with apertures 91a in a ladder shape at positions corresponding to the light emitting units 11, 12 and the light receiving units 13, 14; and a light-transmitting silicone portion 92 disposed on a light transmission hindering portion 91 and block the apertures 91a. The light transmission hindering portion 91 is interposed between the adjacent apertures 91a, therefore entrance of light not propagating inside the head through the silicone portion 92 into the light receiving units 13, 14 can be suppressed, and measurement can be performed with higher accuracy. When a contaminant adheres, only the silicone portion 92 can be replaced. The silicone portion 92 is preferably fixed to a surface of the light transmission hindering portion 91. A fixing method is not particularly limited, but is a heat fusion method or a method using an adhesive or a pressure-sensitive adhesive. As silicone used for the silicone portion 92, the same kind as the silicone portions 17a and 17b described in the first example of the covering portion can be used. The transmittance of light emitted by the light emitting units 11, 12 in terms of a thickness of 1 mm in a silicone portion 92 is preferably 60% or more, and more preferably 80% or more. The light transmission hindering portion 91 is, for example, made of a resin containing a black pigment such as carbon black. The kind of the resin is not particularly limited, but is, for example, polyethylene terephthalate, nylon, or silicone. The transmittance of light emitted by the light emitting units 11, 12 in terms of a thickness of 1 mm in the light transmission hindering portion 91 is preferably one tenth or less with respect to the transmittance of the light in terms of a thickness of 1 mm in the silicone portion 92. As illustrated in FIG. 10, a more preferable form is a form in which the silicone portion 92 is formed of a plurality of sheets slightly larger than each aperture 91a of the light transmission hindering portion 91 and each sheet blocks each aperture 91a to form a gap between the adjacent silicone portions 92.

As illustrated in FIGS. 8 and 9, the connecting unit 50 is preferably disposed on a rear surface of the mounted surface of the sensor unit 10. The connecting unit 50 is, for example, a connector such as a plug-in connector or a ribbon connector or a cable such as a plug-in cable or a ribbon cable. Among these, the connecting unit 50 is preferably a connector. By no use of a cable, a problem that work is hindered because a cable is caught does not occur. The size of the non-invasive monitor for measuring regional saturation of oxygen 1 can be smaller. The connector also serves as a fixing tool for fixing the sensor unit 10 to the main body unit 20. For example, as illustrated in FIG. 2, the connecting unit 50 is connected to a recess type connector (not illustrated) disposed in the main body unit 20 through a through hole 41 disposed in the sensor pressing board 40 and a through hole 71 disposed in a cushion 70 disposed if necessary. The connecting unit 50 may be a ribbon cable (not illustrated) connected to a ribbon connector (not illustrated). In this case, preferably, the ribbon cable is attached to the sensor unit 10 and the ribbon connector is attached to the main body unit 20. Use of the ribbon cable can make attachment and detachment of the sensor unit 10 and the main body unit 20 easier.

The sensor holder 30 is a board-shaped member which can be bent according to the shape of the forehead. A material of the sensor holder 30 is not particularly limited, but for example, is a silicone resin or a nylon resin. Preferably, a double-sided adhesive tape is disposed, or soft elastomer gel-like rubber having reusable self-adhesiveness is disposed on the forehead-side surface of the sensor holder 30. By bringing the sensor holder 30 into closer contact with the forehead, entrance of light from the outside into the light receiving units 13,14 can be suppressed.

The aperture portion 31 is a through hole disposed in the sensor holder 30, and has the light emitting units 11,12 and the light receiving units 13,14 disposed therein. The light emitting surfaces of the light emitting units 11,12 and the light receiving surfaces of the light receiving units 13,14 can be exposed toward the forehead. FIG. 1 illustrates a form in which the aperture portion 31 has a frame shape, but the present invention is not limited thereto, for example, may be a cut-out shape (not illustrated) disposed on an upper end side of the sensor holder 30. A method for holding the sensor unit 10 by the sensor holder 30 is not particularly limited, but for example, is a method for fitting the protrusion 16*a* disposed on the probe cover 16 to the aperture portion 31 or a method for fixing the sensor unit 10 to the sensor holder 30 with an adhesive or a pressure-sensitive adhesive.

As illustrated in FIG. 6, a part or the whole of the forehead-side surface of the sensor unit 10 is on the same surface as the forehead-side surface of the sensor holder 30. Not illustrated, but a part or the whole of the forehead-side surface of the sensor unit 10 may protrude from the forehead-side surface of the sensor holder 30 toward the forehead-side. Protrusion toward the forehead-side can bring about closer contact with the forehead. For example, when the sensor unit 10 has a cross sectional structure illustrated in FIG. 8, a form in which a part of the forehead-side surface of the sensor unit 10 is on the same surface as the forehead-side surface of the sensor holder 30 or protrudes is a form in which the light emitting surfaces of the light emitting units 11,12 and the light receiving surfaces of the light receiving units 13,14 are on the same surface as the forehead-side surface of the sensor holder 30 or protrude, or a form in which the frame portion 18 surrounding the light emitting units 11,12 and the light receiving units 13,14 is on the same surface as the forehead-side surface of the sensor holder 30 or protrudes. For example, when the sensor unit 10 has a cross sectional structure illustrated in FIG. 9, the form is a form in which the silicone portions 17*a* and 17*b* are on the same surface as the forehead-side surface of the sensor holder 30 or protrude.

The sensor pressing board 40 is a board-shaped member which can be bent according to the shape of the forehead. A material of the sensor pressing board 40 is not particularly limited, but for example, is a nylon resin or a silicone resin. The sensor pressing board 40 is disposed between the sensor unit 10 and the main body unit 20, and holds the sensor unit 10 toward the sensor holder 30.

The non-invasive monitor for measuring regional saturation of oxygen 1 according to the present invention preferably further includes a cushion 70 interposed between the main body unit 20 and the sensor pressing board 40. By bringing the sensor unit 10 into closer contact with the forehead, entrance of light from the outside into the light receiving unit can be suppressed, and measurement can be performed with higher accuracy. As illustrated in FIG. 2, in the cushion 70, a surface on a side of the main body unit 20 is planar, and a surface on a side of the sensor pressing board 40 has a concave surface shape. A material of the cushion 70 is not particularly limited, but for example, is urethane foam.

The main body unit 20 includes a housing. A material of the housing is not particularly limited, but for example, is a hard resin such as an ABS resin. The main body unit 20 is disposed in front of the forehead when being mounted on the head. As illustrated in FIG. 3, the main body unit 20 preferably has a center mark 22. The position of the center mark 22 in a lateral direction of the forehead is on the virtual straight line L (illustrated in FIG. 7). An operator can easily recognize the positions of the right light receiving unit 13 (illustrated in FIG. 7) and the left light receiving 14 (illustrated in FIG. 7) using the center mark 22 as a guide. By mounting the monitor by matching the center mark 22 with the center portion in a lateral direction of the forehead of a patient, the oxygen saturation of the right brain and left brain can be measured more securely. The center mark 22 is not particularly limited, but for example, as illustrated in FIG. 3, is obtained by subjecting the main body unit 20 to printing of a substantially rhombic shape and disposing the vertexes of the substantially rhombic shape on the virtual straight line L (illustrated in FIG. 7). The center mark 22 may be a printed dot or line, or may be obtained by embossing on the virtual straight line L (illustrated in FIG. 7).

The computation processing unit (not illustrated) is, for example, a central processing unit (CPU). The computation processing unit (not illustrated) is incorporated in the housing. The computation processing unit (not illustrated) calculates a mixed oxygen saturation of the brain blood based on a detection signal detected by the sensor unit 10. A method for calculating a mixed oxygen saturation by the computation processing unit is, for example, described in Patent Literatures 1 and 2. In measurement of a regional saturation of oxygen of a patient by near-infrared spectroscopy, a deoxyhemoglobin concentration is high in a state indicating a low oxygen saturation level in the brain of the patient. That is, in a wavelength at which deoxyhemoglobin is absorbed largely, an optical signal is weak and is easily influenced by an electrical noise generated by a surrounding electric or electronic device. The computation processing unit preferably subjects the weak optical signal in the state indicating a low oxygen saturation level (a state in which a deoxyhemoglobin concentration is high) to analog-digital conversion. In this case, in order to improve a signal-noise ratio (S/N ratio), deoxyhemoglobin of a high concentration can be measured with high accuracy by disposing an amplifier directly in a photoelectric conversion element to eliminate superimposition of external electrical noise.

The display unit 21 is preferably disposed on a front surface of the housing. The display unit 21 displays a computation processing result by the computation processing unit. The computation processing result is, for example, a graph indicating changes over time in an oxygen saturation of the right brain blood, an oxygen saturation of the left brain blood, and a mixed oxygen saturation of the brain blood. The display unit 21 preferably has a structure in which a direction for viewing display contents can be optionally reversed vertically and horizontally such that a person watching a monitor can confirm the display contents easily at the position without changing the standing position.

A power source unit (not illustrated) is, for example, a battery such as a disposable primary battery, a secondary battery which can be used repeatedly by charging, or a small fuel battery, or an external AC power source. These may be used singly, or may be used in combination of two or more kinds thereof. The power source unit is preferably a battery. Incorporation of a battery in the housing can further improve portability. The power source unit (not illustrated) supplies power to the sensor unit 10, the computation processing unit, and the display unit 21.

The main body unit 20 preferably has an alarm structure (not illustrated). The alarm structure displays a measurement result on the display unit 21 and emits a primary alarm sound when a regional saturation of oxygen ($rSO_2$) measurement value is, for example, 30% or less, and the alarm structure displays a measurement result on the display unit 21 and emits a secondary alarm sound when the measurement value is, for example, 25% or less. A measurement value as a reference to emit an alarm sound is not limited to 30% or 25%, but the setting can be changed arbitrarily. Preferably, the alarm sound has a plurality of sound sources such that the alarm sound can be easily distinguished from an alarm sound emitted by another medical device, and the sound source can be selected and changed arbitrarily.

The main body unit 20 preferably includes a terminal for outputting a computation processing result to an external apparatus. The main body unit 20 preferably has a structure for storing, accumulating, and recording the computation processing result in an incorporated recording medium and recording the computation processing result in a recording medium which can be taken outside. The incorporated recording medium is, for example, a flash memory. The recording medium which can be taken outside is, for example, a SD memory card or a USB memory. Various kinds of data can be input into a monitor apparatus of regional saturation of oxygen ($rSO_2$) installed in a hospital to which a patient has been transported. As a result, continuous data of a regional saturation of oxygen of a patient in an emergency site can be monitored continuously even after the patient is transported to a hospital, and this can largely contribute to increase in an emergency life-saving rate of a patient, increase in a cardiopulmonary resuscitation rate, and increase in a social rehabilitation rate of a patient after life-saving.

FIG. 11 is a diagram illustrating a state in which an outer headband is lifted. The headband 60 mounts the main body unit 20 on the head detachably. As illustrated in FIG. 2, preferably, the headband 60 includes an inner headband 61 connected to the main body unit 20, an outer headband 62 connected to the outside of the inner headband 61, and a connecting portion 63 connecting the outer headband 62 to the inner headband 61 so as to be able to be tightened or loosened, the inner headband 61 includes a slide groove portion 61a, the connecting portion 63 includes a shaft portion 63b engaging with the slide groove portion, and as illustrated in FIG. 11, the headband 60 can lift the outer headband 62 around the shaft portion 63b and can adjust the position of the outer headband 62 by sliding the shaft portion 63b along the slide groove portion 61a and matching the headband with the size of the head. The monitor can be mounted on a patient more easily.

The inner headband 61 is mounted on a side of the head of a patient. A material of the inner headband 61 is not particularly limited, but for example, is a nylon resin or a silicone resin. The inner headband 61 includes the slide groove portion 61a. The slide groove portion 61a is disposed in a length direction of the inner headband 61. The slide groove portion 61a is preferably a through hole penetrating in a thickness direction of the inner headband 61. A cushion 64 is preferably disposed on a patient-side surface of the inner headband 61. A material of the cushion 64 is not particularly limited, but for example, is urethane foam.

The outer headband 62 is mounted over a side of the head of a patient to the back of the head. A material of the outer headband 62 is not particularly limited, but for example, is a nylon resin or a silicone resin. A cushion 65 is preferably disposed on a patient-side surface of the outer headband 62. A material of the cushion 65 is not particularly limited, but for example, is urethane foam.

As illustrated in FIG. 2, the connecting portion 63 preferably includes a helical head portion 63a and the shaft portion 63b. The connecting portion 63 has a tightening and loosening structure. For example, the tightening and loosening structure provides a nut (not illustrated) engaging with the slide groove 61a slidably in the slide groove 61a, and screws a lower end of the shaft portion 63b into the nut. The outer headband 62 can be lifted around the shaft portion 63b by turning the helical head portion 63a in a loosening direction, the shaft portion 63b can slide along the slide groove 61a, and the outer headband 62 is fixed to the inner headband 61 by turning the helical head portion 63a in a tightening direction in a state in which the outer headband 62 is disposed at a predetermined position.

FIG. 12 is a diagram illustrating a state in which the monitor is mounted on a person having a small head. FIG. 13 is a diagram illustrating a state in which the monitor is mounted on a person having a large head. Next, a method for mounting the non-invasive monitor for measuring regional saturation of oxygen 1 on a patient will be described with reference to FIGS. 11 to 13. First, as illustrated in FIG. 11, an operator mounts a sensor unit surely on the cranium (frontal lobe) of a patient in a state in which the outer headband 62 is lifted upward, and then restores the outer headband 62 to a horizontal state. Subsequently, as illustrated in FIGS. 12 and 13, the operator adjusts the position of the outer headband 62 by sliding the shaft portion 63b along the slide groove portion 61a and matching the headband with the size of the head. Finally, the operator fixes the outer headband 62 to the inner headband 61 by turning the helical head portion 63a in a tightening direction to mount the non-invasive monitor for measuring regional saturation of oxygen 1 on a patient. Thereafter, the operator starts measurement of a regional concentration of oxygen.

FIG. 14 is a diagram illustrating a state in which a tightening tool is tightened. FIG. 15 is a diagram illustrating a state in which a tightening tool is loosened. The non-invasive monitor for measuring regional saturation of oxygen 1 according to the present invention preferably further includes a tightening tool 80 connected to the sensor pressing board 40. By bringing the sensor unit into closer contact with the forehead by tightening the sensor pressing board 40 with the tightening tool 80 after mounting the non-invasive monitor for measuring regional saturation of oxygen 1 on a patient, entrance of light from the outside into the light receiving unit can be suppressed, and measurement can be performed with higher accuracy. The tightening tool 80 is only required to have a structure which can be tightened and loosened, and the structure is not particularly limited. An example of the structure of the tightening tool 80 is a structure in which a belt portion 81 and a lock portion 82 are included as illustrated in FIG. 14, the belt portion 81 is fixed to a predetermined position by engagement between the belt portion 81 and the lock portion 82, and tightening by the belt portion 81 can be loosened by releasing the lock portion 82 as illustrated in FIG. 15. The belt portion 81 preferably protrudes out of the headband 60. A tightening work can be performed more easily. For example, a form in which the belt portion 81 protrudes out of the headband 60 is a form in which the belt portion 81 is connected to both ends of the sensor pressing board 40 in a lateral direction of the forehead and the belt portion 81 protrudes out of the headband 60 from a through hole 62a disposed in the outer headband 62 through the slide groove portion 61a of the inner headband 61.

Next, an action of the non-invasive monitor for measuring regional saturation of oxygen 1 will be described. First, the light emitting units 11,12 sequentially output laser light having a predetermined wavelength (for example, 730 nm or 810 nm) based on a signal indicated by CPU (not illustrated). The laser light is emitted from a light emitting surface toward the forehead, and enters the head. The laser light which has entered the head propagates while being scattered in the head and absorbed by a component to be measured, and a part of the light reaches an optical detection position. The laser light which has reached the optical detection position is detected by the light receiving units 13,14. Each of the light receiving units 13,14 generate a photocurrent corresponding to the intensity of the detected laser light. These photocurrents are converted into a voltage signal (detection signal) by a preamplifier (not illustrated), and these voltage signals are converted into digital signals by an A/D conversion circuit.

Subsequently, the computation processing unit (for example, CPU) calculates a hemoglobin oxygen saturation (TOI) based on digital signals $D(1)$ to $D(N)$. CPU calculates a temporal relative change amount of an oxygenated hemoglobin concentration ($\Delta O_2 Hb$) using at least one digital signal among the digital signals $D(1)$ to $D(N)$, and calculates one or both of a temporal relative change amount of a deoxygenated hemoglobin concentration ($\Delta HHb$) and a temporal relative change amount of the total hemoglobin concentration which is the sum of these amounts ($\Delta cHb$), if necessary. CPU removes a frequency component smaller than a predetermined frequency $f_0$ among frequency components contained in these relative change amounts ($\Delta cHb$, $\Delta O_2 Hb$, $\Delta HHb$) by filtering. These relative change amounts after filtering ($\Delta cHb$, $\Delta O_2 Hb$, $\Delta HHb$) and time-series data indicating these amounts are displayed on the display unit 21.

FIGS. 1 to 15 illustrate a form in which a pair of the light emitting units 11,12 and the light receiving units 13,14 is disposed in linear symmetry with respect to a lateral direction of the forehead, but the present invention is not limited thereto, but for example, may be a form in which the light emitting unit 11 and the light receiving unit 13 are present only on the right with respect to the lateral direction of the forehead or a form in which the light emitting unit 12 and the light receiving unit 14 are present only on the left with respect to the lateral direction of the forehead. A form in which the number of the light receiving unit 13 or the light receiving unit 14 is three has been described, but the present invention is not limited by the number of the light receiving units 13,14, and for example, the number of the light receiving unit 13 or the light receiving unit 14 may be one, two, or four or more.

FIG. 16 is a schematic diagram illustrating a modification example of a main body unit. As illustrated in FIG. 16, the main body unit 20 preferably has a button 23. The button 23 is, for example, a power button 23a or a reset button 23b. The button 23 is a press button or an icon displayed on a touch panel. FIG. 3 illustrates a form in which the main body unit 20 includes one display unit 21, but the present invention is not limited thereto. For example, as illustrated in FIG. 16, a first display unit 21a for displaying right brain information including a graph indicating changes over time in an oxygen saturation of the right brain blood and a mixed oxygen saturation of the right brain blood, and a second display unit 21b for displaying left brain information including a graph indicating changes overtime in an oxygen saturation of the left brain blood and a mixed oxygen saturation of the left brain blood may be disposed. In this way, by displaying the right brain information and the left brain information separately, an operator can determine the right brain information and the left brain information more surely and instantaneously. The display unit 21 (21a and 21b) may display a remaining battery capacity or time in addition to a mixed oxygen saturation of the brain blood.

REFERENCE SIGNS LIST

1 non-invasive monitor for measuring regional saturation of oxygen
10 sensor unit
11 light emitting unit (right light emitting unit)
12 light emitting unit (left light emitting unit)
13 light receiving unit (right light receiving unit)
14 light receiving unit (left light receiving unit)
13a,14a light receiving unit for a shallow portion
13b,14b light receiving unit for a deep portion
15 printed circuit board
16 probe cover
16a protrusion
17 covering portion
17a,17b silicone portion
17c light transmission hindering portion
18 frame portion
21 display unit
20 main body unit
21 display unit
21a first display unit
21b second display unit
22 center mark
23 button
23a power button
23b reset button
30 sensor holder
31 aperture portion
40 sensor pressing board
41 through hole
50 connecting unit
60 headband
60 headband
61 inner headband
61a slide groove portion
62 outer headband
63 connecting portion
63a helical head portion
63b shaft portion
64 cushion
65 cushion
70 cushion
71 through hole
80 tightening tool
81 belt portion
82 lock portion
91 light transmission hindering portion
91a aperture
92 silicone portion

The invention claimed is:

1. A non-invasive monitor for measuring regional saturation of oxygen for measuring an oxygen saturation of a brain blood stream continuously in a non-invasive manner by mounting the monitor on a person's head, comprising:

a sensor unit including a printed circuit board on which a light emitting unit for irradiating a surface of the forehead of the head with light of 650 to 1000 nm and a light receiving unit for receiving light which has been emitted by the light emitting unit and has propagated inside the head are mounted, wherein the sensor unit is a board-shaped member that is bent according to the shape of the forehead;

a main body unit disposed in front of the forehead when being mounted on the head, including a computation processing unit for calculating a mixed oxygen saturation of the brain blood based on a detection signal detected by the sensor unit, a display unit for displaying a computation processing result by the computation processing unit, and a power source unit for supplying power to the sensor unit, the computation processing unit, and the display unit;

a sensor holder for holding the sensor unit while the light emitting unit and the light receiving unit are disposed in an aperture portion, having a board shape abutting on the forehead and including the aperture portion penetrating in a board thickness direction thereof, wherein the sensor holder is a board-shaped member that is bent according to the shape of the forehead;

a sensor pressing board for holding the sensor unit toward the sensor holder, disposed between the sensor unit and the main body unit, wherein the sensor pressing board is a board-shaped member that is bent according to the shape of the forehead;

a connecting unit for electrically connecting the sensor unit and the main body unit; and a headband for mounting the main body unit on the head detachably, wherein the sensor holder, the sensor unit, the sensor pressing board, and the main body unit are integrated by being stacked in this order from the forehead-side, wherein the light emitting unit and the light receiving unit are disposed such that a light emitting surface of the light emitting unit and a light receiving surface of the light receiving unit face the forehead-side, and a part or the whole of the forehead-side surface of the sensor unit is on the same surface as the forehead-side surface of the sensor holder or protrudes from the forehead-side surface of the sensor holder toward the forehead-side, wherein the sensor unit includes a right light emitting unit and a left light emitting unit as the light emitting unit and includes a right light receiving unit and a left light receiving unit as the light receiving unit, and the left light receiving unit, the left light emitting unit, the right light emitting unit, and the right light receiving unit are disposed in this order in a lateral direction of the forehead, wherein the left light emitting unit and the right light emitting unit are disposed in linear symmetry with a virtual straight line between the left light emitting unit and the right light emitting unit as a symmetric axis, wherein the left light receiving unit and the right light emitting unit are disposed in linear symmetry with the virtual straight line as a symmetric axis, wherein the right light emitting unit and the right light receiving unit is for measuring the oxygen saturation of the right brain, and the left light emitting unit and the left light receiving unit is for measuring the oxygen saturation of the left brain, and wherein the main body unit has a center mark, and the position of the center mark in a lateral direction of the forehead is on the virtual straight line.

2. The non-invasive monitor for measuring regional saturation of oxygen according to claim 1, further comprising a cushion interposed between the main body unit and the sensor pressing board.

3. The non-invasive monitor for measuring regional saturation of oxygen according to claim 1, wherein
the headband includes an inner headband connected to the main body unit, an outer headband connected to the outside of the inner headband, and a connecting portion connecting the outer headband to the inner headband so as to be able to be tightened or loosened,
the inner headband includes a slide groove portion,
the connecting portion includes a shaft portion engaging with the slide groove portion, and
the headband can lift the outer headband around the shaft portion and can adjust the position of the outer headband by sliding the shaft portion along the slide groove portion and matching the headband with the size of the head.

4. The non-invasive monitor for measuring regional saturation of oxygen according to claim 1, further comprising a tightening tool connected to the sensor pressing board.

5. The non-invasive monitor for measuring regional saturation of oxygen according to claim 1, wherein the connecting unit is a connector.

6. The non-invasive monitor for measuring regional saturation of oxygen according to claim 1, wherein
the sensor unit includes a covering portion for covering a part or the whole of the forehead-side surface of the sensor unit, and
the covering portion is configured to transmit the light at least in a silicone portion covering the light emitting surface-side of the light emitting unit and the silicone portion covering the light receiving surface-side of the light receiving unit.

7. The non-invasive monitor for measuring regional saturation of oxygen according to claim 6, wherein
the covering portion includes a light transmission hindering portion at least between the silicone portion covering the light emitting unit and the silicone portion covering the light receiving unit, and in comparison with unit thickness, a material of the light transmission hindering portion is able to transmit light at a maximum of ten percent of a material of the silicone portion.

8. The non-invasive monitor for measuring regional saturation of oxygen according to claim 1, wherein the sensor unit includes a light receiving unit which receives light that has passed through a shallow layer of the brain and a light receiving unit which receives light that has passed through a deep layer of the brain as the light receiving unit.

9. The non-invasive monitor for measuring regional saturation of oxygen according to claim 2, wherein the cushion has a planar surface on a side of the main body unit and a concave-shaped surface on a side of the sensor pressing board.

10. The non-invasive monitor for measuring regional saturation of oxygen according to claim 4, wherein the tightening tool includes a belt portion connected to the sensor pressing board and a lock portion which fixes the belt portion and has a structure in which the belt portion is fixed to a predetermined position by engagement between the belt portion and the lock portion and tightening by the belt portion can be loosened by releasing the lock portion.

11. The non-invasive monitor for measuring regional saturation of oxygen according to claim 5, wherein the connector is connected to a recess type connector disposed in the main body unit through a through hole disposed in the sensor pressing board, and the connector also serves as a fixing tool for fixing the sensor unit to the main body unit.

* * * * *